(12) United States Patent
Crouzen et al.

(10) Patent No.: US 7,135,597 B2
(45) Date of Patent: Nov. 14, 2006

(54) PROCESS FOR THE PREPARATION OF MONOCHLOROACETIC ACID

(75) Inventors: Jeroen Crouzen, ES Arnhem (NL); Johannes Joseph Gorissen, BM Velp (NL); Cornelis Johannes Govardus Van Strien, SJ Elst (NL)

(73) Assignee: Akzo Nobel N.V., Arnhem (NL)

( * ) Notice: Subject to any disclaimer, the term of this patent is extended or adjusted under 35 U.S.C. 154(b) by 0 days.

(21) Appl. No.: 10/529,144

(22) PCT Filed: Oct. 2, 2003

(86) PCT No.: PCT/EP03/10944

§ 371 (c)(1), (2), (4) Date: Apr. 19, 2005

(87) PCT Pub. No.: WO2004/033408

PCT Pub. Date: Apr. 22, 2004

(65) Prior Publication Data

US 2005/0272953 A1    Dec. 8, 2005

(30) Foreign Application Priority Data

Oct. 11, 2002   (EP)   ................................. 02079252

(51) Int. Cl.
*C07C 51/00* (2006.01)
(52) U.S. Cl. .................................................. 562/603
(58) Field of Classification Search ...................... None
See application file for complete search history.

(56) References Cited

U.S. PATENT DOCUMENTS

| | | |
|---|---|---|
| 4,281,184 A | 7/1981 | Spaziante et al. |
| 4,939,294 A | 7/1990 | Agreda et al. |
| 5,013,407 A | 5/1991 | Nocca et al. |
| 5,449,801 A | 9/1995 | Barnum et al. |
| 5,705,711 A | 1/1998 | Preston |
| 5,741,953 A | 4/1998 | Preston |
| 5,811,597 A | 9/1998 | Hwan et al. |

FOREIGN PATENT DOCUMENTS

| | | |
|---|---|---|
| BE | 714 767 A | 11/1968 |
| EP | 0 547 939 A1 | 6/1993 |
| EP | 0 755 706 A1 | 1/1997 |
| EP | 0 978 501 A | 2/2000 |
| EP | 1 013 325 A1 | 6/2000 |
| FR | 2 664 180 A1 | 1/1992 |
| JP | A 60-58932 | 4/1985 |
| NL | C 1009499 | 1/2000 |
| SU | 1801963 A1 | 3/1993 |
| WO | WO 83/03825 | 11/1983 |
| WO | WO 96/17817 | 6/1996 |
| WO | WO 00/78700 A2 | 12/2000 |
| WO | WO 01/17939 A1 | 3/2001 |
| WO | WO 01/41894 A1 | 6/2001 |
| WO | WO 02/10094 A1 | 2/2002 |

OTHER PUBLICATIONS

Stichlmair, "Reactive Distillation Processes," Chem. Ing.-Tech., pp. 1507-1516, 70(12), 1998 w/ abstract.
Mikitenko, "Reactive Distillation: Principle, Applications and Prospects," Pet. Tech., pp. 34-38, 1986 w/ abstract.
Yaohua, "Uses of Monochloroacetic Acid and Current Status of its Industrial Production, " Hubei Nationalities Chemical Institute and Environmental Engineering Institute, Enshi 445000, TQ225.3 A, 1004-0404(2003)02-0038-, 2003.
Yonggang et al., "Study on Production of MCA by anhydride-catalyzed chlorination of acetic acid," Tianjin Research and Designing Institute of Chemical Industry, Tianjin 300131;2: Institute of Chemical Technology of Tianjin University, Tianjin 300072, TQ225.3 A, 1008-133X(2001)02-0023-04, Feb. 2001.
Yongxue, One-step method for preparing highly pure monochloroacetic acid, Tanghai county Agrochemical Works, Tangshan 063200, vol. 16, No. 4, 1994.

*Primary Examiner*—Paul A. Zucker
(74) *Attorney, Agent, or Firm*—Oliff & Berridge, PLC

(57) ABSTRACT

The invention pertains to a process for the production of monochloroacetic acid from chlorine and acetic acid in the presence of a catalyst by reactive distillation. The process and the required reactive distillation apparatus is much less complex than conventional reactors and yields a monochloroacetic acid product having a low content of over-chlorinated products.

12 Claims, 1 Drawing Sheet

PROCESS FOR THE PREPARATION OF MONOCHLOROACETIC ACID

BACKGROUND

The invention relates to a process for the preparation of monochloroacetic acid from chlorine and acetic acid in the presence of a catalyst.

Such a process for the preparation of monochloroacetic acid is commonly known and generally makes use of a bubble column reactor in which a mixture of acetic acid (HAc) and acetic anhydride is present and through which mixture chlorine gas bubbles are led. Acetic anhydride immediately is converted with chlorine gas into acetyl chloride which is the catalyst for this process. The process generally is conducted at a pressure of from 3 to 5 barg and a temperature of from 115 to 155° C. In the bubble column reactor, monochloroacetic acid (MCA) and gaseous HCl are formed together with by-products of which dichloroacetic acid (DCA) and trichloroacetic acid are examples. Part of the catalyst acetyl chloride leaves the bubble column reactor as a gas and is recovered to a large extent in a catalyst recovery section. Such a catalyst recovery section is generally complex, as it comprises columns, coolers, heat exchangers, pumps and piping, and consequently is expensive in respect of maintenance and equipment costs.

After the MCA-containing reaction product mixture has passed the bubble column reactor(s) and the catalyst recovery section, DCA is still present in a significant amount, which is typically about 5%. The MCA/DCA-containing product mixture is subsequently led to a reduction unit where DCA is reduced with hydrogen in the presence of a hydrogenation catalyst, e.g. a Pd-based catalyst. This catalyst not only reduces DCA, but it also reduces MCA to some extent, which is of course undesirable. Moreover, such a reduction unit and its operation is very expensive, and this adds to the costs of the MCA end-product.

The low-boiling components are then removed from the MCA by conventional vacuum distillation.

SUMMARY

It is an object of the present invention to provide a process which is less complex in terms of the hardware of the manufacturing plant and which yields an MCA product having a low DCA content relative to conventional processes using a bubble column reactor.

The present invention is a process for the preparation of monochloroacetic acid from chlorine and acetic acid in the presence of a catalyst by reactive distillation.

More in particular, the invention pertains to a process wherein a reactive distillation apparatus is used, the apparatus comprising a reactive distillation column comprising at least one column internal, which column is on one side connected to a cooler unit and on the other side connected to a reboiler, and which apparatus is provided with a first inlet for supplying chlorine, and optionally other gasses or volatile liquids such as hydrochloric acid or nitrogen, a second inlet for supplying acetic acid, a third inlet for supplying the catalyst, a first outlet for removing MCA-containing product, and a second outlet for recovering the catalyst, whereby the first inlet and the first outlet are positioned closer to the reboiler than the second inlet and the third inlets, and whereby the second outlet is connected to the cooler unit, the process comprising the steps of supplying chlorine via the first inlet, supplying acetic acid via the second inlet, supplying the catalyst via the third inlet, recovering the catalyst via the second outlet, and removing the MCA-containing product via the first outlet.

DETAILED DESCRIPTION OF EMBODIMENTS

Figure 1:
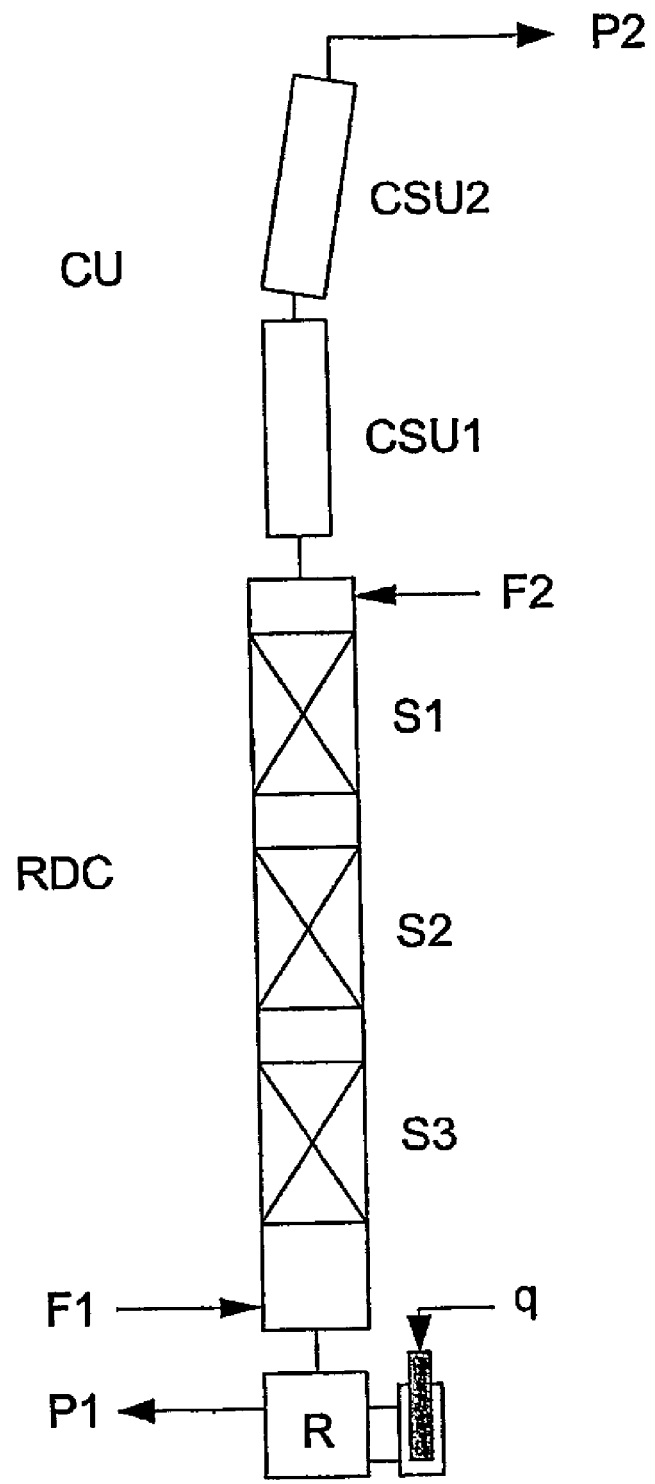
FIG. 1 is a schematic representation of a reactive distillation apparatus of the present invention.

Reactive distillation provides a completely new route for the preparation of MCA integrating the chlorination reaction and distillation in one operation. A reactive distillation apparatus is much less complex than a conventional MCA production unit for chlorinating acetic acid comprising at least a reacting and a catalyst recovering section. As a consequence, the costs of the apparatus itself as well as the maintenance costs thereof are appreciably lower compared to conventional production units, especially considering the expensive construction materials required for handling MCA. The simplicity of the apparatus also enables easy operation, a high reliability, and reproducibility. Moreover, with the process of the present invention it is possible to optimize the contact time of the reactants, such as chlorine, and/or the products, more in particular of MCA, and the reactant composition so as to minimize the further chlorination of MCA to in particular DCA. In this way, the selectivity to MCA may be increased and the formation of undesirable DCA is suppressed. As low DCA formation is achievable, reduction of DCA to MCA may no longer be required. Furthermore, only a relatively small fraction of the catalyst is able to leave the reactive distillation column via the cooler unit so that the catalyst recovery section can be left out entirely or made less complex. A further advantage is that, since the catalyst does not leave via the bottom of the column (i.e. at or in the vicinity of the reboiler), only an absorption column may be required for removal of the catalyst via the cooler unit.

The catalyst can be any suitable catalyst for the chlorination reaction. The preferred catalyst is acetyl chloride. Either acetyl chloride or a precursor thereof, e.g. acetic anhydride, is fed to the reactive distillation column via the third inlet. In case the anhydride is used, it is, when in contact with chlorine or hydrochloric acid, converted to acetyl chloride. As acetic anhydride is expensive, the catalyst is generally recovered as much as possible. With the process of the invention the catalyst loss per ton MCA is significantly lower compared to conventional processes. Consequently, a smaller amount of acetic anhydride per ton MCA is needed, thus reducing the catalyst cost.

In one embodiment of the invention process, a mixture of the catalyst and acetic acid is added to the column. In such case, only the second inlet will be sufficient and a third inlet may be obsolete.

The process of the present invention typically depends on a number of reaction parameters such as the pressure in the column, the mass ratio of chlorine to acetic acid, the mass ratio of acetic anhydride to acetic acid added, the number and/or type of trays of the reactive distillation column, the temperature of the cooler unit and/or reboiler, and the liquid residence time in the said column.

The process may be conducted at any suitable pressure at which the chlorination reaction takes place. During the reaction, the pressure in the reboiler is preferably at least $0.5 \cdot 10^5$ Pa, more preferably at least $1 \cdot 10^5$ Pa, and most preferably at least $1.5 \cdot 10^5$ Pa, and preferably at most $10 \cdot 10^5$ Pa, more preferably at most $9 \cdot 10^5$ Pa and most preferably at most 8·10⁵ Pa. A higher pressure may be advantageous as the reactive distillation apparatus may be made smaller in size, and thus the apparatus will be cheaper.

Another relevant reaction parameter is the mass ratio of chlorine to acetic acid as supplied to the column. Preferably, this mass ratio is at least 0.1, preferably at least 0.5, and most preferably at least 1.0, and preferably at most 2.0, more preferably at most 1.8, and most preferably at most 1.5. It is noted that in general the higher the fraction of chlorine in the total feed the higher the selectivity to undesirable overchlorinated products such as DCA and trichloroacetic acid.

It is noted that the concentration of chlorine in the column, for example above a tray, may become so high that the safety of the process is impaired. In order to reduce or diminish this safety risk, chlorine may be diluted with a diluting gas selected from the group consisting of hydrochloric acid, an inert gas such as nitrogen or helium, a volatile liquid or a mixture thereof. Preferably, the diluting gas comprises hydrochloric acid. Hydrochloric acid has the further advantage of reducing the degree of overchlorination of MCA, and thus improving the selectivity to the desired product MCA. Yet another advantage of hydrochloric acid is that this compound is already present in the column and that no new compound is introduced.

The amount of diluting gas added depends on the pressure of the reaction. At lower pressures more diluting gas is required than at higher pressures in order to produce monochloroacetic acid in a safe manner. A skilled person will be able to determine the minimum amount of diluting gas that needs to be added with respect to the supplied amount of chlorine in order to operate safely.

Generally, the mole ratio of diluting gas to chlorine as supplied to the column is at least 0.05, preferably at least 0.1, and most preferably at least 0.15, and preferably at most 9.0, more preferably at most 5, and most preferably at most 3. Preferably, the mole ratio of hydrochloric acid to chlorine as supplied to the column is at least 0.05, preferably at least 0.1, and most preferably at least 0.15, and preferably at most 9.0, more preferably at most 5, and most preferably at most 3.

Also the mass ratio of acetic anhydride to acetic acid is a reaction parameter which may significantly influence the chlorination reaction. Preferably, this mass ratio is at least 0.0001, more preferably at least 0.0003, and most preferably 0.001, and preferably at most 0.25, more preferably at most 0.22, and most preferably at most 0.20. It is noted that, if it is assumed that the chlorine-acetic acid mass ratio is constant, a lower acetic anhydride-acetic acid mass ratio will lead to a lower selectivity to DCA with respect to MCA. Furthermore, a relatively higher catalyst fraction generally leads to a higher reaction rate.

The reactive distillation column comprises at least one column internal. Examples of such a column internal are a tray or packing. The number of trays of the reactive distillation column is also an important reaction parameter as these determine the effectiveness of the separation process of the reactants and products that takes place in the column, simultaneously with the reactions. Preferably, the number of trays in the column is at least 1, more preferably at least 2, and most preferably at least 5, and preferably at most 80, more preferably at most 60, most preferably at most 40. A skilled person further would understand that the size of the trays and the volume of the liquid, which each tray can contain, can vary and will also influence the reaction and/or separation effectiveness.

Desirably, the column will have trays, but any gas liquid contacting device might be suitable. Alternatively, suitable conventional packing, such as Raschig rings, Pall rings, saddles or structured packing of any kind might be used instead of trays. The different sections in the column might be equipped with different types of packing and/or trays.

A further parameter is the liquid residence time in the column. The liquid residence time determines the conversion rate of acetic acid to MCA and of MCA to overchlorinated products. The longer MCA remains in the reactive distillation column the higher the chance that MCA will react with chlorine to give DCA or trichloroacetic acid. The liquid residence time is influenced by the above-mentioned reaction parameters and can thus be optimized by varying at least one of the above parameters. The residence time is chosen so as to obtain an optimal conversion and selectivity level. Preferably, the residence time in the column is at least 0.01 hour, more preferably at least 0.1 hour and most preferably at least 0.4 hour, and preferably at most 5 hours, more preferably at most 4 hours, and most preferably at most 3 hours.

The temperature of the reboiler and the cooler unit is chosen such that the chlorination reaction takes place in the column. The reboiler is heated to a temperature at which a vapor is formed which is then transported to the reactive distillation column, thus providing heat to the column. A mixture comprising at least one of MCA and acetic acid may be present in the reboiler. The temperature of the reboiler is preferably at least 60° C., more preferably at least 80° C., and most preferably at least 120° C., and preferably at most 320° C., more preferably at most 280° C., and most preferably at most 240° C.

The temperature of the cooler unit is lower than the reboiler temperature, and is chosen such that low-boiling products, such as hydrogen chloride, can leave the column, and that the reactants and high-boiling products, such as MCA condensate and remain in the column. The cooler unit can comprise just one cooler unit or may comprise a plurality of cooler sub-units, whereby each sub-unit has a specific temperature. A preferred embodiment of such a cooler unit comprises a first and a second cooler sub-unit. Preferably, the temperature of the first cooler sub-unit is at least 0° C., more preferably at least 10° C., and most preferably at least 20° C., and preferably at most 80° C., more preferably at most 70° C., and most preferably at most 60° C. Preferably, the temperature of the second cooler sub-unit is at least −80° C., more preferably at least −60° C., and most preferably at least −50° C., and preferably at most 30° C., more preferably at most 10° C., and most preferably at most −10° C.

It is advantageous to carry out the process of the invention with a reactive distillation apparatus wherein the second inlet is positioned close to the cooler unit. In this way, the acetic acid which is provided via the second inlet is introduced above the reaction zone.

Although a single first inlet is preferred, a plurality of first inlets may also be used in accordance with the present invention. In order to control the chlorination injection into the column even better, it is possible to provide a plurality of first inlets which are distributed throughout the length of the reactive distillation column. Through each first inlet the same amount of chlorine per hour can be added to the column. It is, however, also possible to vary the amount of chlorine per hour for each inlet individually. The added chlorine amounts may be the same during the reaction or may vary, as desired. It is further noted that chlorine and a diluting gas can be added to the column simultaneously via the same inlet, or simultaneously and/or individually via separate inlets. The chlorine concentration may vary for every first inlet.

Analogously, a plurality of second and/or third inlets can be distributed throughout the length of the reactive distillation column. The provision of a plurality of second and/or third inlets can be combined with a plurality of first inlets or with a single first inlet. Preferably, at least one of the second inlets and/or at least one of the third inlets are situated closer to the cooler unit than the first inlet which is closest to the reboiler.

It is also envisaged to provide the column with a plurality of outlets. These outlets can be distributed throughout the length of the reactive distillation column. Preferably, at least one of the outlets are situated closer to the reboiler than the second and/or third inlets.

This means that acetic acid, chlorine and acetic anhydride are continuously added to the distillation column, and that simultaneously the product MCA is continuously removed from the column via the outlet. Preferably this continuous mode of operation is conducted in such a way that the chlorination yield and selectivity remain substantially the same in time during the chlorination reaction.

The invention is illustrated with the following example.

EXAMPLE 1

FIG. 1 shows a schematic representation of a reactive distillation apparatus in accordance with the present invention. A reactive distillation column (RDC) with an internal diameter of 50 mm. consists of three sections with perforated plates, which sections are denoted as S1, S2 and S3. Each section consists of 10 Oldershaw type plates with an operating holdup of 6 ml per stage.

On top of the column a cooler unit CU which comprises two cooler sub-units, i.e. a first cooler sub-unit (CSU1) and a second cooler sub-unit (CSU2), is present. Through CSU1, cooling water (having a temperature of 17° C.) is led. CSU2 is operated with a water/methanol mixture (having a temperature of −20° C.).

The reboiler R is filled with glass beads to minimize the liquid holdup. In the reboiler R, two quartz tubes q (each being able to provide a power of up to 1000 W) act as heat supply for boiling of the reaction mixture within the reboiler.

The first inlet (F1) and the second inlet (F2) are located just below S1 and just above S3, respectively. Samples are taken from the reboiler at sampling point P1 and from the gas leaving sub-unit CSU2 at sampling point P2. The liquid samples taken from P1 were analyzed using HPLC and NMR. From the gas sample taken from P2, the chlorine content is determined by titration.

The following chemicals were used in this example:
acetic acid (>99.8%), ex Fluka,
acetyl chloride (>99.8%), ex Fluka,
hydrogen chloride (>99.9%), ex BOC gases,
chlorine (chlorine 2.7), ex Air Liquide.

The experiment was started by charging 849 gram of acetic acid to the reboiler R and heating the reboiler R until the acetic acid (HAc) boiled up to S1. The heat input as supplied by each quartz tube q was 400 Watt, the temperature in the column had then risen to 120° C. Subsequently, 204 gram of acetyl chloride was added to the column at inlet F2. After acetyl chloride was added, the reflux temperature decreased to 48° C. After this temperature was reached, 92 gram/hour of acetic acid was charged to the column at inlet F2, followed by simultaneously charging chlorine gas at a rate of 0.5 $I_n$/min ($I_n$ refers to normal liter) and hydrogen chloride (HCl) at a rate of 0.5 $I_n$/min to the column at inlet F1.

Frequently, part of the mixture collected in the reboiler was removed from the reboiler while the reaction proceeded. The vapor stream leaving cooler sub-unit CSU2 is first led through two flasks with water to absorb HCl and then led through a flask with caustic soda to destroy chlorine in the vapor stream. The reaction is monitored by (i) periodically measuring the MCA and acetic acid content within the mixture collected in the reboiler R, and (ii) periodically sampling gas coming from CSU2 and determining the chlorine content from P2.

The chlorine fraction in the gas directly relates to the chlorine conversion in the column, i.e. a decrease of one percent in the gas equals two percent chlorine conversion. The bottom product analysis (P1) gives indirect information about the MCA formation rate, since the product is initially diluted with acetic acid present in the reactive distillation column. In Table 1 the measured chlorine content in the off gas (P2) and measured MCA, DCA and HAc amount in the bottom product stream (P1) are tabulated.

TABLE 1

| Time [min] | $Cl_2$ content off gas Mole % | $Cl_2$ conversion [%] | HAc content [wt %] | MCA content [wt %] | DCA content [wt %] |
| --- | --- | --- | --- | --- | --- |
| 8 | 28.5 | 43 | 99.6 | 0.4 | 0 |
| 22 | 25.8 | 48.4 | 99.2 | 0.75 | 0.03 |
| 43 | 25.5 | 49 | 97.8 | 2.14 | 0.08 |
| 86.5 | 18.9 | 62.2 | 91.3 | 8.45 | 0.26 |
| 106 | 21.1 | 57.8 | 90.1 | 9.56 | 0.29 |
| 122.5 | 22.0 | 56 | | | |
| 149 | 25.2 | 49.6 | 85.6 | 13.98 | 0.41 |
| 194 | 27.7 | 44.6 | 81.6 | 17.89 | 0.5 |
| 252 | 29.4 | 41.2 | 77.2 | 22.19 | 0.60 |
| 307 | 30.7 | 38.6 | 72.9 | 26.41 | 0.68 |
| 338 | 30.2 | 39.6 | 70.9 | 28.4 | 0.73 |
| 365 | 29.7 | 40.6 | 71.8 | 27.5 | 0.70 |

Table 1 shows that MCA is produced by using reactive distillation. It furthermore shows that the selectivity towards MCA is relatively high and towards DCA is relatively low.

The invention claimed is:

1. A process for the preparation of monochloroacetic acid from chlorine and acetic acid in the presence of a catalyst by reactive distillation.

2. The process according to claim 1, wherein the reactive distillation is conducted in a reactive distillation apparatus that comprises:
   a reactive distillation column;
   a cooler unit, and
   a reboiler;
   wherein the reactive distillation column comprises at least one column internal, which column internal is on one side connected to the cooler unit and on the other side connected to the reboiler, and
   wherein the reactive distillation apparatus is provided with a first inlet for supplying chlorine, a second inlet for supplying acetic acid, a third inlet for supplying the catalyst, a first outlet for removing the monochloroacetic acid-containing product, and a second outlet for recovering the catalyst, whereby the first inlet and the first outlet are positioned closer to the reboiler than the second and the third inlets, and whereby the second outlet is connected to the cooler unit; and
   wherein the process comprises
   supplying chlorine via the first inlet,
   supplying acetic acid via the second inlet,
   supplying the catalyst via the third inlet, recovering the catalyst via the second outlet, and removing the monochloroacetic acid-containing product via the first outlet.

3. The process according to claim 1, wherein a catalyst is acetyl chloride.

4. The process according to claim 1, wherein a applied pressure is at least $0.5 \cdot 10^5$ and at most $10 \cdot 10^5$ Pa.

5. The process according to claim 1, wherein a mass ratio of chlorine to acetic acid is at least 0.1 and at most 2.0.

6. The process according to claim 1, wherein the catalyst is acetic anhydride and a mass ratio of acetic anhydride to acetic acid is at least 0.0001 and at most 0.25.

7. The process according to claim 1, wherein the column internal is a tray, whereby the number of trays is at least 1 and at most 80.

8. The process according to claim 1, wherein a liquid residence time in the reactive distillation column is at least 0.1 and at most 5 hours.

9. The process according to claim 2, wherein the second inlet is positioned close to the cooler unit.

10. The process according to claim 1, wherein the process is conducted continuously.

11. The process according to claim 1, wherein a diluting gas is added, the diluting gas being selected from the group consisting of hydrochloric acid, an inert gas and a mixture thereof.

12. The process according to claim 11, wherein the inert gas is selected from the group consisting of nitrogen, helium and mixtures thereof.

* * * * *